(12) United States Patent
Reiss

(10) Patent No.: US 6,633,747 B1
(45) Date of Patent: Oct. 14, 2003

(54) ORTHODONTIC APPLIANCE AUDIO RECEIVER

(75) Inventor: Lori K. Reiss, Allentown, PA (US)

(73) Assignee: Lucent Technologies Inc., Murray Hill, NJ (US)

( * ) Notice: Subject to any disclaimer, the term of this patent is extended or adjusted under 35 U.S.C. 154(b) by 448 days.

(21) Appl. No.: 09/614,513

(22) Filed: Jul. 12, 2000

(51) Int. Cl.[7] .................................................. H04Q 7/32
(52) U.S. Cl. ...................... 455/41; 455/66; 455/344; 455/90; 433/5; 433/6; 340/384.1
(58) Field of Search .................... 455/66, 344, 2.01, 455/575, 90, 347, 350, 352, 41; 433/5, 6; 340/384.1

(56) References Cited

U.S. PATENT DOCUMENTS

| | | | | |
|---|---|---|---|---|
| 3,696,297 A | * | 10/1972 | Otero | 455/66 |
| 3,985,977 A | * | 10/1976 | Beaty et al. | 455/66 |
| 4,382,780 A | * | 5/1983 | Kurz | 433/5 |
| 5,326,349 A | * | 7/1994 | Baraff | 433/5 |
| 6,067,006 A | * | 5/2000 | O'Brian | 340/348.1 |

OTHER PUBLICATIONS

Anderson et al., Low power portable communication system with wireless receiver, Mar. 14, 2002, Pub. No. US 2002/003087 A1.*

Chihara et al., Mobile video telephone system, Jun. 6, 2002, Pub. No. 2002/006800 A1.*

* cited by examiner

*Primary Examiner*—William Trost
*Assistant Examiner*—Keith Ferguson

(57) ABSTRACT

An orthodontic appliance audio receiver injects sound into the head and ear cavities of the wearer using vibration, e.g., mandibular (or skull) vibration. Using mandibular vibration, the wearer hears the audio source noiselessly, effortlessly, and without disturbing others, yet provides themselves with entertainment or other audio information. The orthodontia metalwork may be used to form an antenna. Hearing audio (e.g., music) by 'feeling' vibrations from the orthodontic appliance audio receiver encourages a patient to wear their prescribed orthodontia, improving and/or expediting the overall orthodontic therapy. A wireless (or even wired in low cost applications) audio signal receiver is built-in to a retainer, together with a transducer and a power source such as a battery, allowing unlimited transfer of information directly into the wearer's head through their mouth. An appropriate RF transmitter device worn or carried by the user may include a local point-to-point transmitter or a local wireless network device (e.g., a BLUETOOTH piconet), in combination with any audio source (e.g., CD player, cassette player, digital fixed medium player such as an MP3 player, etc.). Alternatively, the RF transmitter may relate to a conventional radio station transmitter.

24 Claims, 8 Drawing Sheets

ORTHODONTIC APPLIANCE AUDIO RECEIVER

BACKGROUND OF THE INVENTION

1. Field of the Invention

This invention relates generally to orthodontic appliances. More particularly, it relates to a novelty orthodontic appliance capable of noiselessly injecting audio into a head of a user.

2. Background

An orthodontic appliance is a device commonly known as a retainer which retains teeth moved during a period of orthodontic treatment. A typical retainer is made of acrylic sections or plates which are placed in a patient's mouth.

Generally speaking, retainers are well known for their use in the treatment of teeth following the removal of fixed appliances. The orthodontic appliance retains the positions of teeth when worn. Orthodontic appliances are removable and worn by a patient in accordance with instructions given by an orthodontist. Orthodontic appliances may be used for anterior teeth only, and/or for teeth of an entire arch, either upper or lower.

Successful results from any retainer depend upon the cooperation of the patient in wearing the retainer for suitable periods of time. Problems such as relapse can occur if the patient fails to wear the orthodontic appliance regularly for a period of time.

Social factors often interfere with a patient's regularity in wearing a prescribed orthodontic appliance. For instance, use of a retainer may often be limited by some patients to nighttime and/or bedtime use because of the reluctance of the patient to wear the retainer in a social setting during the day (e.g., while at school or work). Other users may not want to wear their retainer even at night, e.g., if the user is simply lazy, or if the retainer is perceived as being uncomfortable.

Attempts have been made to make the use of a retainer more fashionable, if not tolerable, by changing the color of the palette plastics. While this may add to the marketability of the retainer, it does not necessarily cure the reluctance of wearer's to use the retainer during daytime functions.

There is a need for a retainer which encourages greater use by the wearer to improve and speed the orthodontic process.

SUMMARY OF THE INVENTION

In accordance with the principles of the present invention, an orthodontic appliance comprises an orthodontic plate, and a radio frequency receiver integrated with the orthodontic plate.

A method of playing audio from an orthodontic appliance in accordance with another aspect of the present invention comprises incorporating a wireless receiver in an orthodontic appliance, and vibrating at least a portion of the orthodontic appliance at an audio frequency.

BRIEF DESCRIPTION OF THE DRAWINGS

Features and advantages of the present invention will become apparent to those skilled in the art from the following description with reference to the drawings, in which.

DETAILED DESCRIPTION OF ILLUSTRATIVE EMBODIMENTS

The present invention relates to the inclusion of entertainment functionality to an orthodontic appliance (i.e., retainer).

An orthodontic appliance audio receiver in accordance with the principles of the present invention is a motivational device that makes the post braces stage of wearing a retainer fun, fashionable, and informational, thus encouraging greater use during the teeth retention phase of orthodontia as well as increasing the social acceptance of the use of a retainer, particularly for school age children.

In accordance with the principles of the present invention, a wireless receiver is built-in to a retainer, allowing unlimited transfer of information directly into the wearer's head through their mouth.

Figure 1:
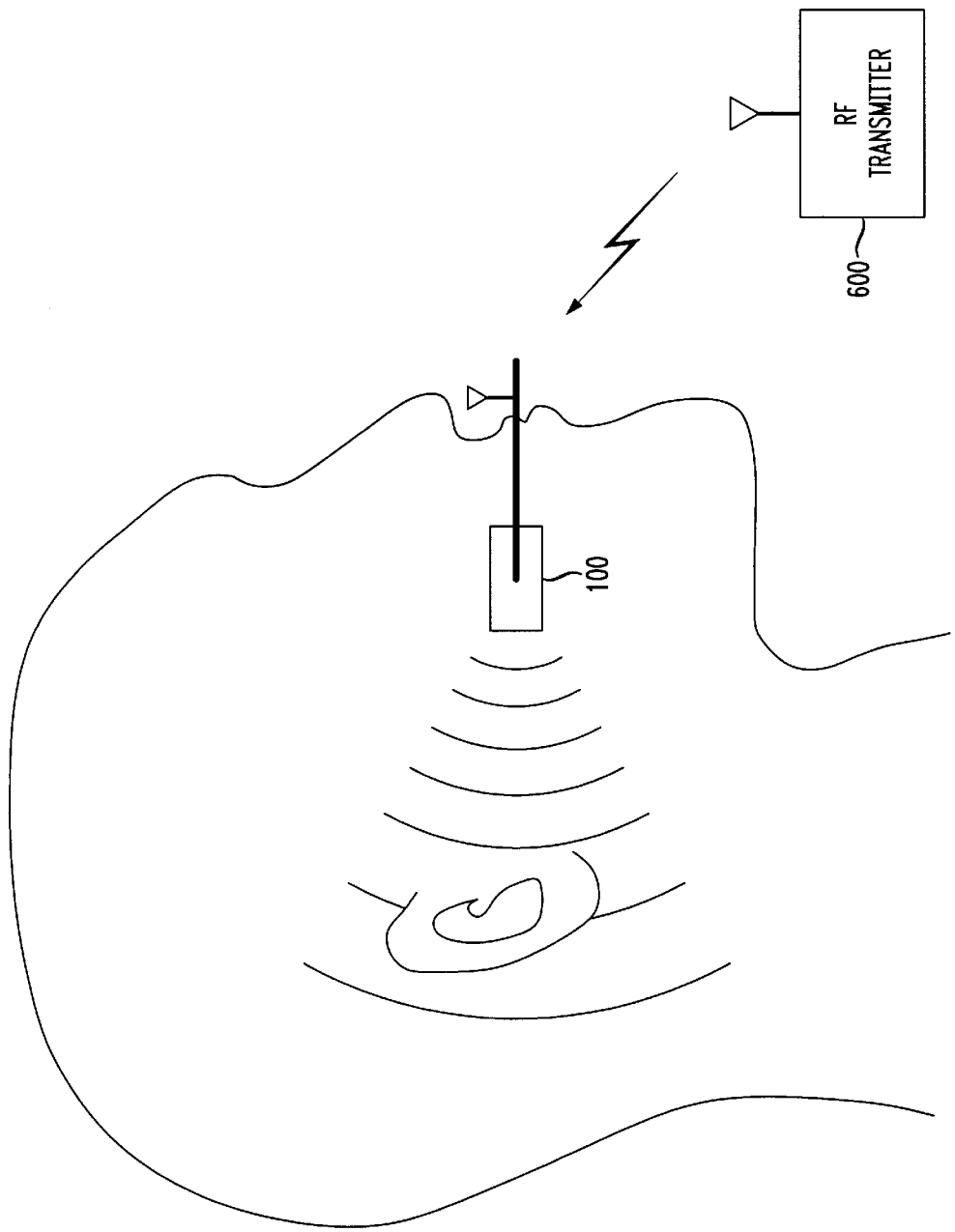
FIG. 1 shows an orthodontic appliance audio receiver in a patient's mouth in communication with an audio signal transmitter (e.g., using radio frequency (RF) analog or digital signals), in accordance with the principles of the present invention.

FIG. 1 shows an orthodontic appliance audio receiver 100 in a patient's mouth in communication with an audio signal transmitter 600 (e.g., using radio frequency (RF) analog or digital signals), in accordance with the principles of the present invention.

In particular, as shown in FIG. 1, an orthodontic appliance audio receiver 100 receives audio signals from an appropriate RF transmitter 600, and soundlessly 'plays' the audio for the wearer only by vibration of the jawbone and/or skull.

Figure 2:
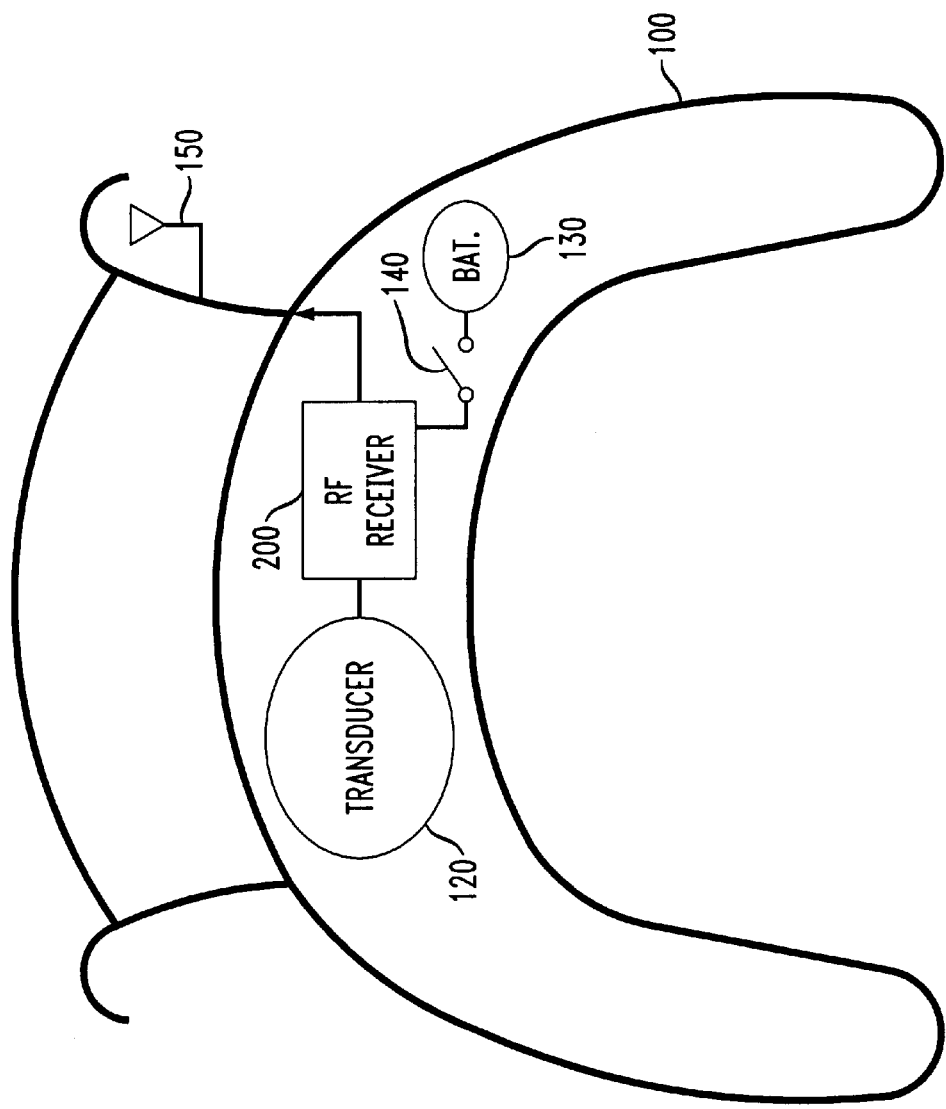
FIG. 2 shows an exemplary orthodontic appliance audio receiver including an RF receiver and a transducer, in accordance with the principles of the present invention.

FIG. 2 is a more detailed depiction of an exemplary orthodontic appliance audio receiver 100 including an RF receiver 200 and a transducer 120, in accordance with the principles of the present invention.

In particular, FIG. 2 shows the use of an orthodontic appliance to provide housing and amplification of a received audio signal. The orthodontic appliance may relate to the upper and/or to the lower bite plate, though it need not actually contact any teeth.

An exemplary embodiment of an orthodontic appliance audio receiver 100 in accordance with the principles of the present invention includes a radio frequency (RF) receiver 200, a transducer 120, and a power source such as a battery 130.

The transducer 120 is implemented into the orthodontic appliance audio receiver 100, and transmits sound directly into the wearer's mouth. The orthodontic appliance audio receiver 100 causes audio reception by audio frequency vibration received by the wearer internally through the jawbone (mandible) or skull to the cochlar structure of the ear. The audio frequency vibration is caused in the plastic encasement of the orthodontic appliance audio receiver 100 by the transducer 120.

The transducer 120 may be any suitable device which converts an electrical signal from the RF receiver 200 into a physical movement to vibrate the plastic orthodontics (and the jawbone and/or skull of the wearer). One suitable transducer 120 is a piezoelectric transducer. Alternatively, the transducer 120 may be a miniature speaker.

Preferably, the transducer 120 is itself resistant to moisture. However, the transducer 120 may be sealed on or in the orthodontic plastic to provide moisture resistance and protection for the transducer 120, RF receiver 200, and battery 130.

The battery 130 may be any suitable but preferably small battery. E.g., a lithium type watch battery or the like may be permanently or removably sealed within the plastic (or other material) of the orthodontia. Alternatively, the acidic nature of saliva may be used to form the basis of a battery while placed in the wearer's mouth.

The RF receiver 200 may be permanently powered ON, e.g., used only when the battery 130 is in place, or may be powered on with a suitable switch 140.

The switch 140 may be a suitable miniature mechanical or electro-mechanical switch. Preferably, the switch 140 is itself water resistant, or is encased within the plastic of the orthodontia such that water (i.e., saliva) does not reach the RF receiver 200 and/or battery 130.

In another embodiment, the switch 140 may be formed electrically and/or mechanically such that it self-powers ON only when in place within the wearer's mouth. For instance, the switch 140 may be placed such that contact and pressure from placement against a tooth holds the switch closed (and powered ON), while removal from the wearer's mouth turns the electronics OFF.

Alternatively, the opposite contact sides of a control switch may be closed by the electrical path formed by electrolytes in saliva, thus allowing automatic powering ON when both contacts are contacting a pool of saliva. The control switch may control a relay, transistor, or other closable circuit between the battery 130 and the RF receiver 200.

Importantly, the orthodontic appliance audio receiver 100 injects sound into the head and ear cavities of the wearer using vibration, e.g., mandibular vibration. Using mandibular vibration, the wearer hears the audio source noiselessly, effortlessly, and without disturbing others, yet provides themselves with entertainment or other audio information.

In accordance with the principles of the present invention, the added novelty of hearing audio (e.g., music) by 'feeling' vibrations from the orthodontic appliance audio receiver 100 encourages a patient to wear their prescribed orthodontia, improving and/or expediting the overall orthodontic therapy.

The orthodontic appliance audio receiver 100 receives audio signals from an appropriate RF transmitter 600. The RF transmitter 600 is a local device worn or otherwise proximate by the wearer. Thus, the RF transmitter 600 communicates with the orthodontic appliance audio receiver 100 using direct, point-to-point analog or digital RF communications.

On a larger scale, the RF transmitter 600 may be installed in a house or small office. For instance, in longer range applications (e.g., 100 meters), a wireless network (e.g., a piconet) may be established between the RF transmitter 600 and one or more orthodontic appliance audio receivers 100. A suitable wireless piconet is defined by the BLUETOOTH standard. Information regarding the BLUETOOTH standard is available, e.g., at www.bluetooth.com.

On a very large scale, the RF transmitter 600 may be an AM or FM radio station, with the orthodontic appliance audio receiver 100 receiving conventional AM or FM stations.

The metalwork inherently within the orthodontia (e.g., formed plastic) of the orthodontic appliance audio receiver 100 may also be used to provide an antenna 150 for the RF receiver 200. Of course, a separate antenna either internal or external to the orthodontia is also within the principles of the present invention.

Figure 3:
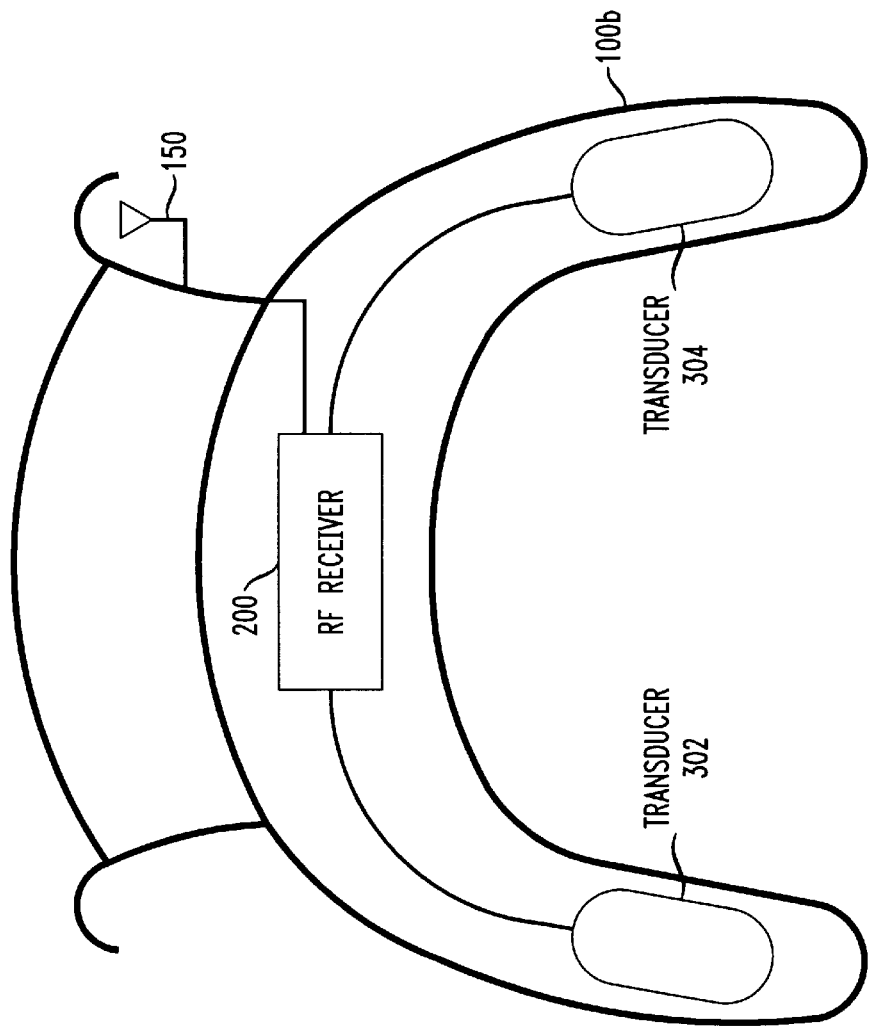
FIG. 3 shows another embodiment of an orthodontic appliance audio receiver including an RF receiver and two transducers corresponding to each ear, in accordance with the principles of the present invention.

FIG. 3 shows another embodiment of an orthodontic appliance audio receiver 100b including an RF receiver 200 and two transducers 302, 304 each corresponding to an ear, in accordance with the principles of the present invention.

In particular, as shown in FIG. 3, more than one transducer 302, 304 may be implemented within or on the orthodontia. As shown in FIG. 3, the transducers 302, 304 are located in a more rearward location than as shown in FIG. 2, providing a closer arrangement to the ears of the user. Thus, softer vibration of the transducers 302, 304 may be used as opposed to the use of a single transducer centrally and forward located as shown in FIG. 2.

Figure 4:
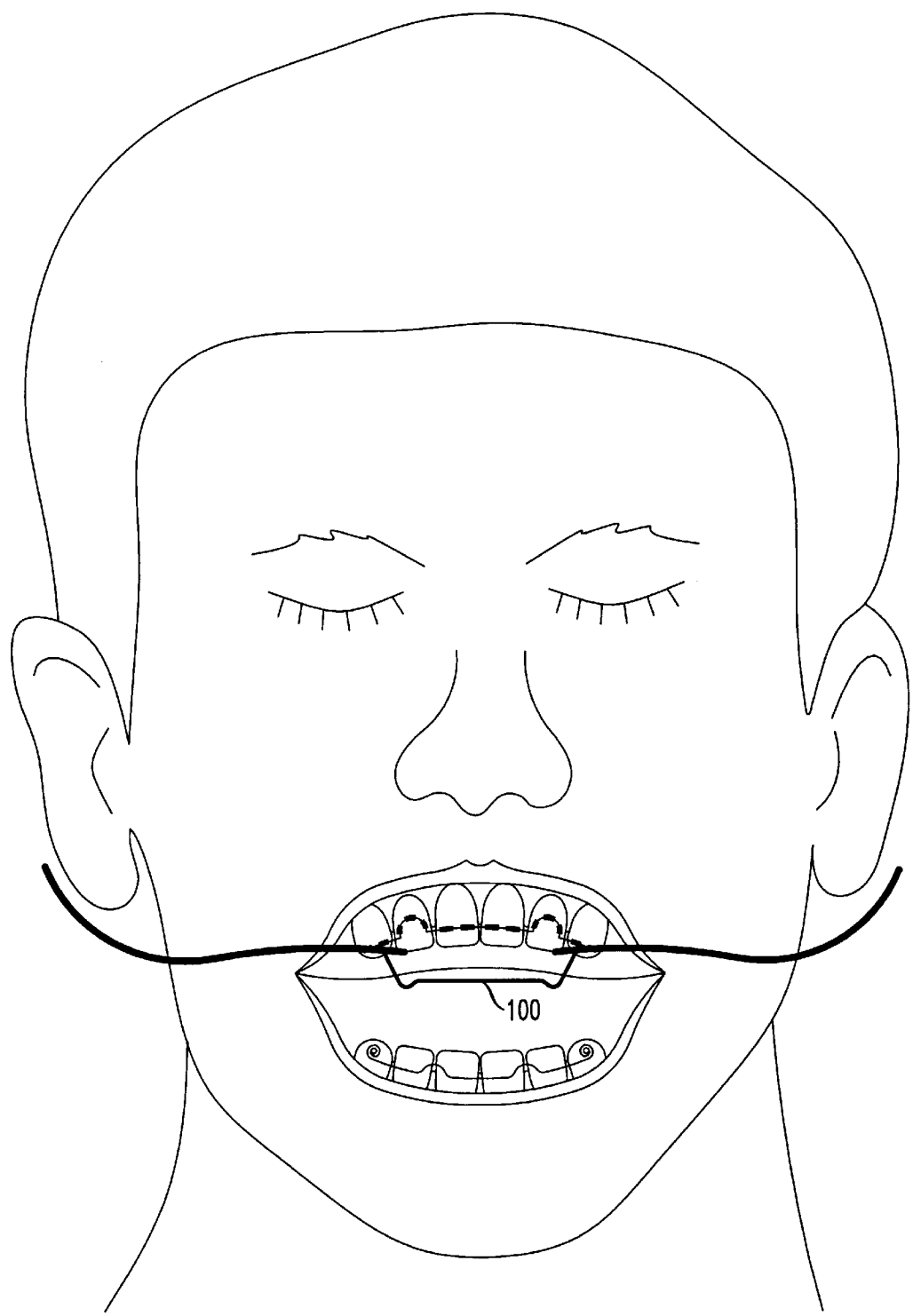
FIG. 4 shows an exemplary placement of the orthodontic appliance audio receiver shown in FIGS. 1–3, in accordance with the principles of the present invention.

FIG. 4 shows an exemplary placement of the orthodontic appliance audio receiver 100 shown in FIGS. 1–3, in accordance with the principles of the present invention.

In particular, the orthodontic appliance audio receiver 100 may be placed within the plastic (or other material) forming the orthodontia which is worn around and/or behind teeth and/or against the roof of the wearer's mouth.

Figure 5:
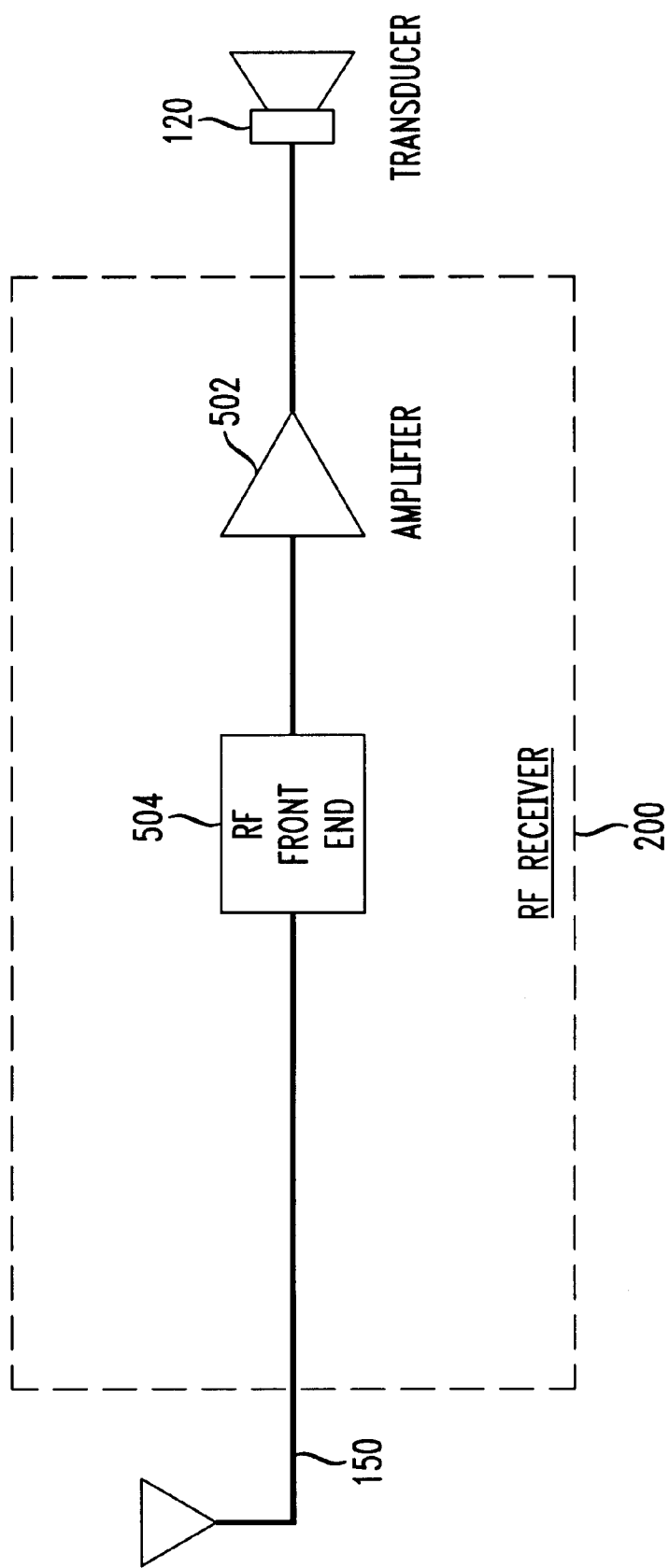
FIG. 5 shows an exemplary schematic of the RF receiver shown in FIGS. 2 and 3.

FIG. 5 shows an exemplary schematic of the RF receiver 100 shown in FIGS. 2 and 3.

In particular, as shown in FIG. 5, the RF receiver 100 includes an appropriate RF front end 504 to receive an appropriate analog or digital audio signal received by an antenna 150 (e.g., the retainer strap), and an amplifier 502 to drive the transducer(s) 120.

The RF front end 504 of the RF receiver 200, if forming an AM and/or FM radio, may be that used in any miniature portable wireless receiver, e.g., those worn in the ear by swimmers.

Moreover, the amplifier 502 may have a fixed gain thereby providing a fixed volume control, thus leaving volume control to the RF transmitter 600. Alternatively, the amplifier 502 may have a variable gain in either digital or analog form. If a digital volume is provided, appropriate user UP and DOWN controls may be provided on the surface of the orthodontic appliance audio receiver 100 to allow the user to raise or lower the volume. Alternatively, if an analog volume is provided (e.g., a resistor pot), an appropriate adjustment may be made accessible to the user (e.g., when the orthodontic appliance audio receiver 100 is removed from the wearer's mouth).

Of course, the volume of the transducer 120 may be fixed at an appropriate level via the amplifier in the receiver, eliminating the need for a volume control at the orthodontic appliance audio receiver 200, but instead leaving volume control to the particular audio source providing audio to the RF transmitter 600.

Figure 6:
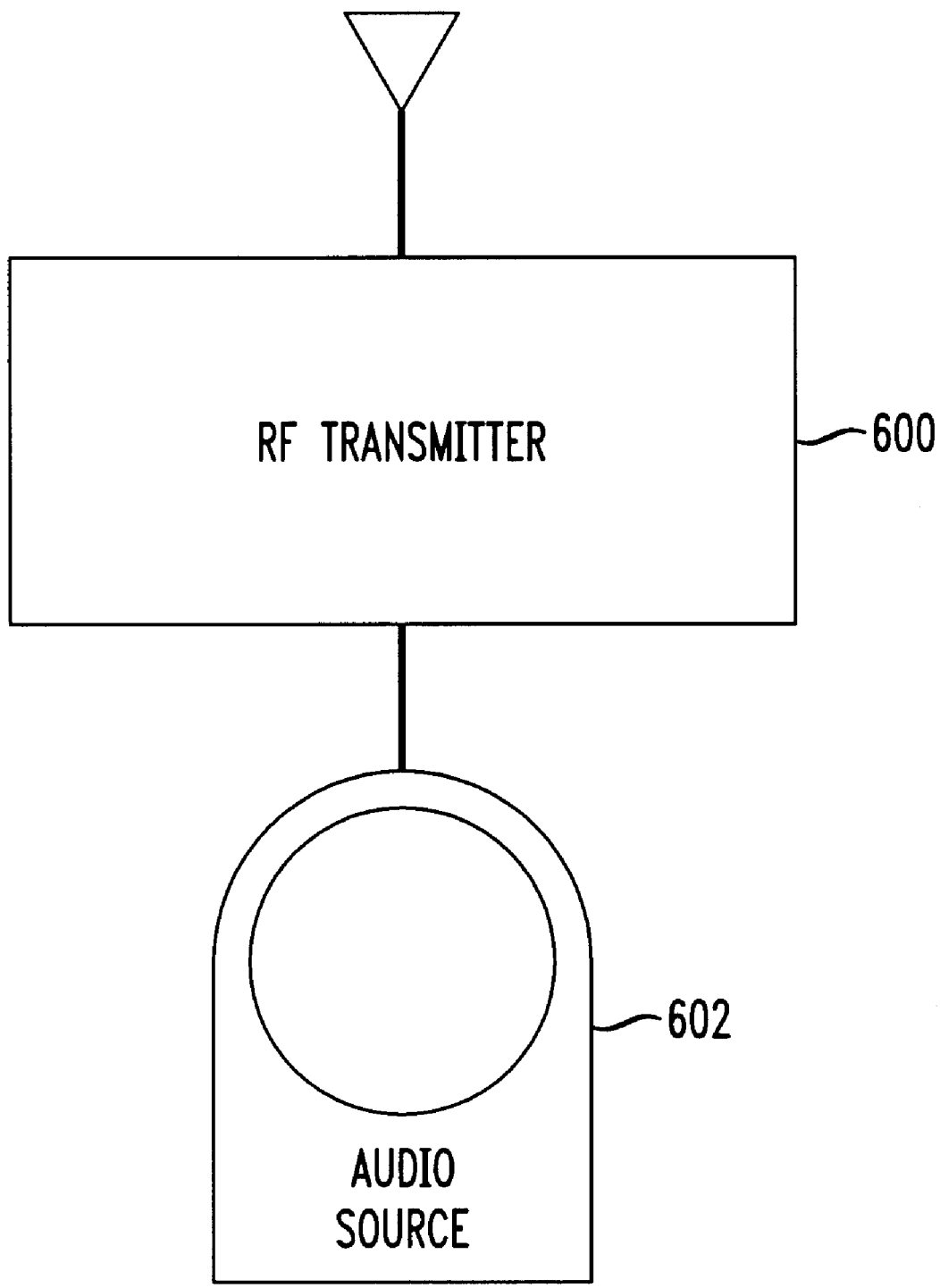
FIG. 6 shows the use of a separate audio source to provide an audio signal stream to the RF transmitter, in accordance with the principles of the present invention.

FIG. 6 shows the use of a separate audio source 602 to provide an audio signal stream to the RF transmitter 600, in accordance with the principles of the present invention.

In particular, the RF transmitter 600 may include an audio source therein. For instance, the RF transmitter 600 may be part of a compact disc (CD) player and/or AM/FM radio tuner.

Figure 7:
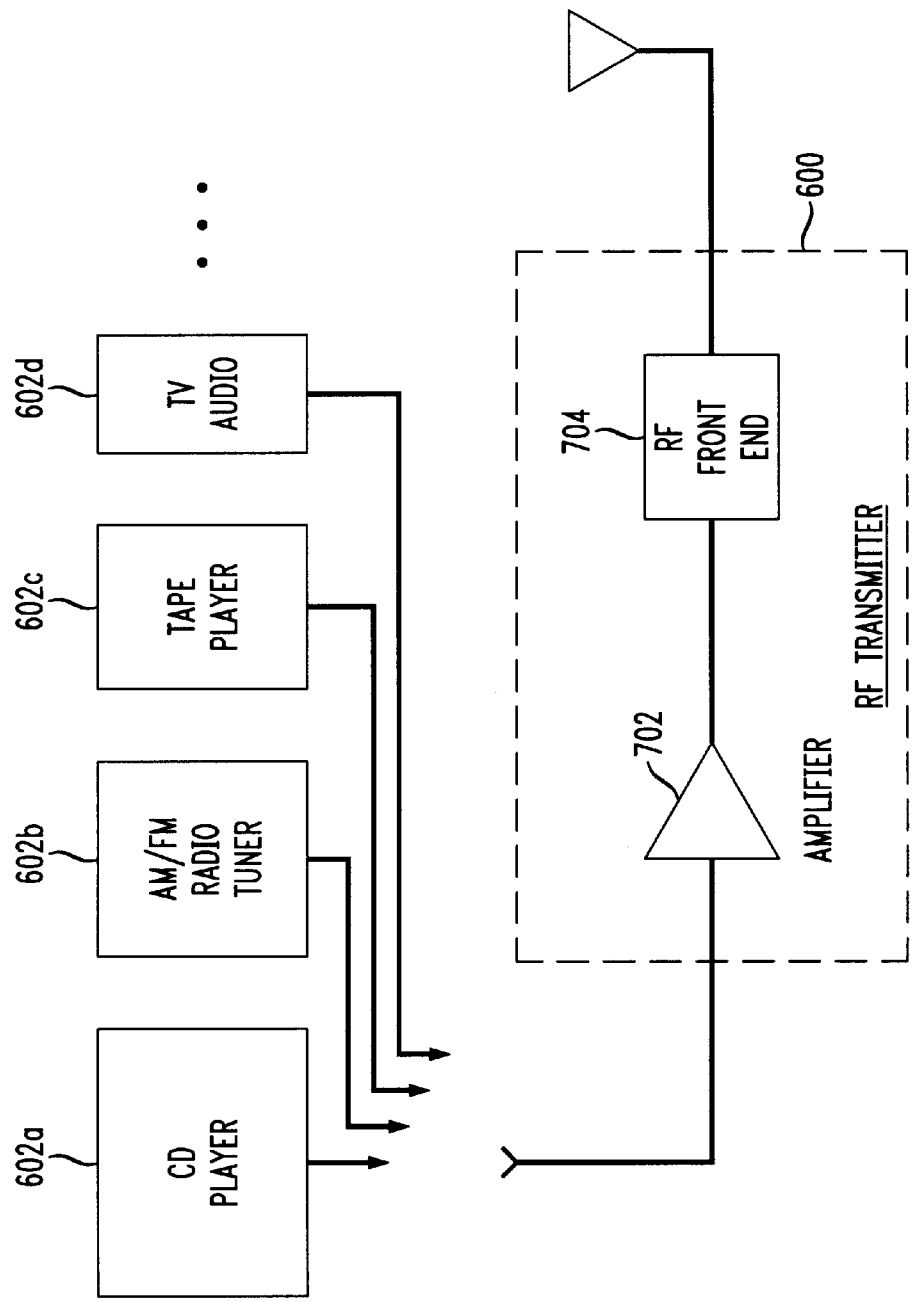
FIG. 7 shows an exemplary schematic of the RF transmitter shown in FIG. 1, depicted receiving an audio signal stream from any suitable audio source, e.g., from a CD player, AM/FM radio, cassette tape player, television audio, etc., in accordance with the principles of the present invention.

FIG. 7 shows an exemplary schematic of the RF transmitter 600 shown in FIG. 1, depicted receiving an audio signal stream from any suitable external audio source, e.g., from a CD player 602a, AM/FM radio tuner 602b, cassette tape player 602c, television audio 602d, etc., in accordance with the principles of the present invention.

In particular, the audio source to the RF transmitter 600 may be any suitable sound source. For instance, the audio source may be an AM and/or FM radio tuner 602b, an audio cassette tape player 602c, a compact disk (CD) player 602a, a fixed medium digital audio player such as an MP3 player, a DVD player, a television audio path 602d, a voice recorder, a computer file (e.g., ".wav" file), a PDA, an instructional lesson from tape, etc.

The RF transmitter 600, if a local point-to-point device as shown in FIG. 7, may include an appropriate amplifier 702 (e.g., a pre-amplifier), and an appropriate RF front end 704 to match the RF front end 504 in the RF receiver 200.

The principles of the present invention relate equally to the use of a piconet to establish connectivity between an audio source and the orthodontic appliance audio receiver 100.

Figure 8:
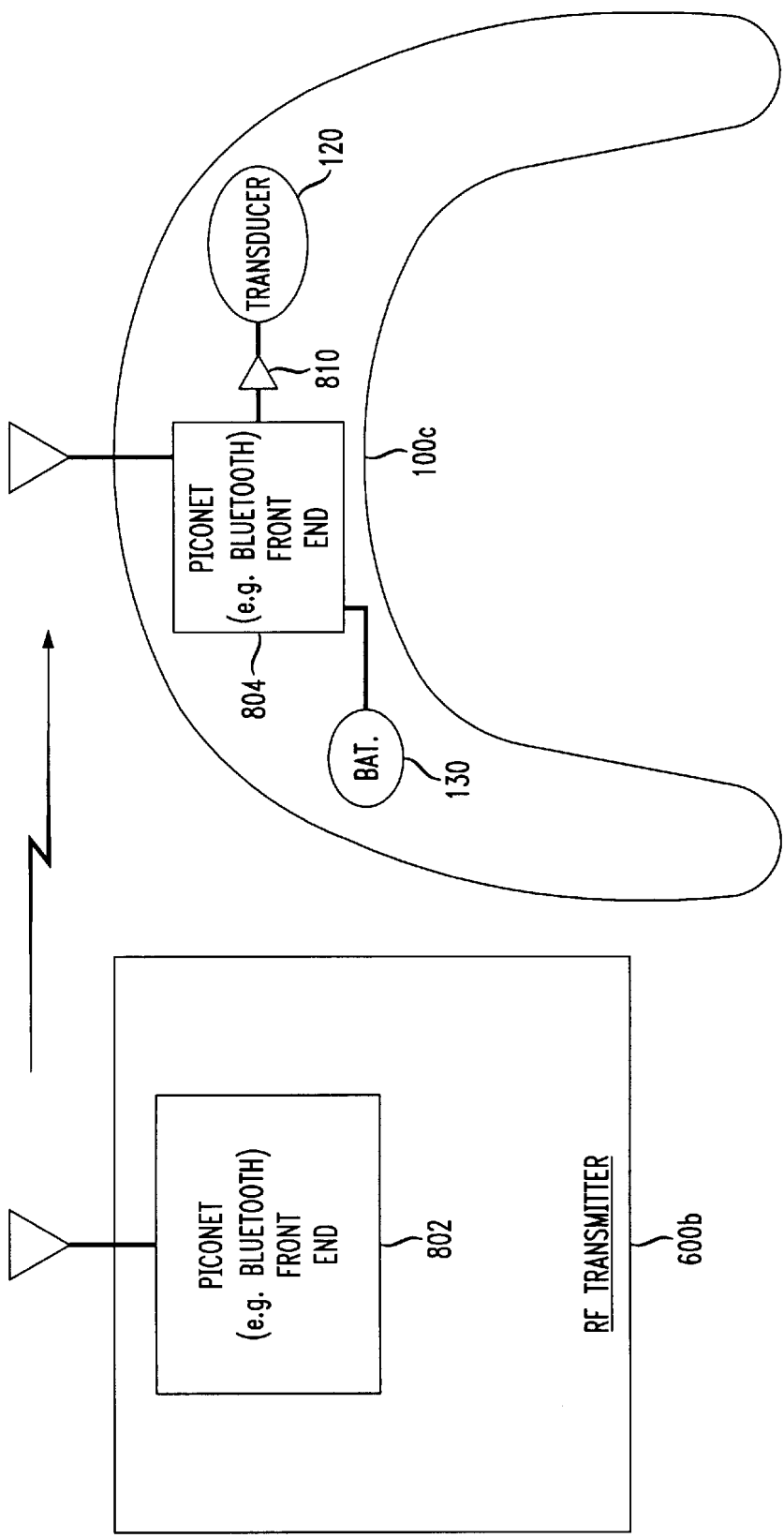
FIG. 8 shows the use of a wireless piconet network such as BLUETOOTH to provide transport of an audio stream from an audio source to an orthodontic appliance audio receiver, in accordance with the principles of the present invention.

FIG. 8 shows the use of a wireless piconet network such as BLUETOOTH to provide transport of an audio stream from an audio source to an orthodontic appliance audio receiver, in accordance with the principles of the present invention.

In particular, as shown in FIG. 8, the RF front end 504 of the RF receiver 200 shown in FIG. 5 may be replaced with an appropriate piconet (e.g., BLUETOOTH) front end 804, and the RF front end 704 of the RF transmitter 600 shown in FIG. 7 may be replaced with an appropriate piconet (e.g., BLUETOOTH) front end 802. In this embodiment, an audio signal is transmitted between the RF transmitter 600b and an orthodontic appliance audio transceiver 100c as digital data packets in a piconet transmission.

Additional functionality may be added to the orthodontic appliance audio transceiver 100 to create additional entertainment or other functionality. For instance, alarm clock functionality may be added such as a sleep mode, or a 'wake to music' mode. Using a sleep mode, the orthodontic appliance audio transceiver 100 may be worn to bed, and placed in a sleep mode wherein the music automatically turns itself off after a preset amount of time, e.g., after 30 minutes. Using a 'wake to music' mode, a clock may be internally maintained and set using appropriate user interface buttons on the RF transmitter 600 such that the music will be played through the retainer at the preset time in the morning to wake up the overnight retainer wearer.

While the invention has been described with reference to the exemplary embodiments thereof, those skilled in the art will be able to make various modifications to the described embodiments of the invention without departing from the true spirit and scope of the invention.

What is claimed is:

1. An orthodontic appliance, comprising:
   an orthodontic plate; and
   a radio frequency receiver integrated with said orthodontic plate for receiving an entertainment signal and transfer of said entertainment signal to said orthodontic plate.

2. The orthodontic appliance according to claim 1, wherein:
   said radio frequency receiver is encased within said orthodontic plate.

3. The orthodontic appliance according to claim 1, wherein:
   said radio frequency receiver is at least one of an AM and FM radio receiver.

4. The orthodontic appliance according to claim 1, wherein:
   said radio frequency receiver is a BLUETOOTH transceiver.

5. The orthodontic appliance according to claim 1, further comprising:
   a radio frequency transmitter remote from said orthodontic plate transmitting an audio signal to said radio frequency receiver.

6. The orthodontic appliance according to claim 5, wherein:
   said audio signal is digitized for transmission.

7. The orthodontic appliance according to claim 5, further comprising at least one of the following in communication with said radio frequency transmitter:
   a CD player;
   an AM radio tuner;
   an FM radio tuner;
   a cassette tape player;
   a television;
   a fixed medium digital audio player;
   a DVD player;
   a voice recorder;
   a computer audio output path; and
   a PDA.

8. The orthodontic appliance according to claim 5, further comprising:
   a fixed medium digital audio player.

9. The orthodontic appliance according to claim 8, wherein said fixed medium digital audio player comprises:
   an MP3 player.

10. The orthodontic appliance according to claim 1, further comprising:
    a transducer fixed to said orthodontic plate.

11. The orthodontic appliance according to claim 10, wherein said transducer comprises:
    a piezoelectric device.

12. The orthodontic appliance according to claim 10, wherein said transducer comprises:
    a speaker.

13. The orthodontic appliance according to claim 1, further comprising:
    a sleep module to automatically turn off music from being played by said orthodontic appliance.

14. The orthodontic appliance according to claim 1, further comprising:
    a wake to music module to automatically start playing music in said orthodontic appliance at a preset time.

15. A method of playing audio from an orthodontic appliance, comprising:
    operating a wireless receiver in an orthodontic appliance; and
    vibrating at least a portion of said orthodontic appliance at an audio frequency to convey an entertainment signal to a wearer of said orthodontic appliance.

16. The method of playing audio from an orthodontic appliance according to claim 15, wherein:

said vibrating is accomplished using a piezoelectric device.

17. The method of playing audio from an orthodontic appliance according to claim 16, further comprising:

receiving an audio signal from a wireless transmitter.

18. The method of playing audio from an orthodontic appliance according to claim 17, wherein:

said received audio signal is received from a radio station.

19. A method of playing audio from an orthodontic appliance, comprising:

operating a wireless receiver in an orthodontic appliance;

vibrating at least a portion of said orthodontic appliance at an audio frequency; and automatically powering up a wireless receiver in said orthodontic appliance when said orthodontic appliance is placed in a mouth of a user.

20. Apparatus for playing audio from an orthodontic appliance, comprising:

wireless receiver means incorporated with an orthodontic appliance for receiving an audio signal; and vibrating means for vibrating at least a portion of said orthodontic appliance to convey an entertainment signal to a wearer of said orthodontic appliance.

21. The apparatus for playing audio from an orthodontic appliance according to claim 20, wherein said vibrating means comprises:

a piezoelectric device.

22. The apparatus for playing audio from an orthodontic appliance according to claim 21, further comprising:

means for receiving an audio signal from a wireless transmitter.

23. The apparatus for playing audio from an orthodontic appliance according to claim 22, wherein:

said received audio signal is received from a radio station.

24. A method of playing audio from an orthodontic appliance, comprising:

wireless receiver means incorporated with an orthodontic appliance for receiving an audio signal;

vibrating means for vibrating at least a portion of said orthodontic appliance; and means for automatically powering up a wireless receiver in said orthodontic appliance when worn said orthodontic appliance is placed in a mouth of a user.

* * * * *